United States Patent
Carr et al.

(10) Patent No.: US 12,214,335 B2
(45) Date of Patent: Feb. 4, 2025

(54) SYNGAS AND METHOD OF MAKING THE SAME

(71) Applicant: HYCO1, Inc., Houston, TX (US)

(72) Inventors: Gregory Carr, Houston, TX (US); David DeVilliers, Katy, TX (US); Kurt A. Dieker, Maize, KS (US)

(73) Assignee: HYCO1, Inc., Houston, TX (US)

( * ) Notice: Subject to any disclaimer, the term of this patent is extended or adjusted under 35 U.S.C. 154(b) by 0 days.

(21) Appl. No.: 18/448,326

(22) Filed: Aug. 11, 2023

(65) Prior Publication Data

US 2023/0381750 A1    Nov. 30, 2023

Related U.S. Application Data

(63) Continuation of application No. PCT/US2022/038733, filed on Jul. 28, 2022.

(60) Provisional application No. 63/203,784, filed on Jul. 30, 2021.

(51) Int. Cl.
| | |
|---|---|
| *B01J 23/78* | (2006.01) |
| *B01J 35/40* | (2024.01) |
| *B01J 37/02* | (2006.01) |
| *B01J 37/03* | (2006.01) |
| *B01J 37/08* | (2006.01) |
| *B01J 38/06* | (2006.01) |
| *C01B 3/40* | (2006.01) |
| *C01B 32/40* | (2017.01) |

(52) U.S. Cl.
CPC ............. *B01J 23/78* (2013.01); *B01J 35/40* (2024.01); *B01J 37/0201* (2013.01); *B01J 37/0236* (2013.01); *B01J 37/03* (2013.01); *B01J 37/082* (2013.01); *B01J 38/06* (2013.01); *C01B 3/40* (2013.01); *C01B 32/40* (2017.08); *C01B 2203/0238* (2013.01); *C01B 2203/1058* (2013.01); *C01B 2203/1082* (2013.01); *C01B 2203/1241* (2013.01)

(58) Field of Classification Search
None
See application file for complete search history.

(56) References Cited

U.S. PATENT DOCUMENTS

| | | | |
|---|---|---|---|
| 2014/0145117 | A1 | 5/2014 | Bal et al. |
| 2015/0307352 | A1 | 10/2015 | Kumar |

(Continued)

FOREIGN PATENT DOCUMENTS

| | | |
|---|---|---|
| CN | 102083526 | 6/2011 |
| CN | 116715198 | 9/2023 |
| WO | WO-2023009760 A1 | 2/2023 |

OTHER PUBLICATIONS

"International Application Serial No. PCT/US2022/038733, International Search Report mailed Dec. 6, 2022", 4 pgs.

(Continued)

*Primary Examiner* — Coris Fung
*Assistant Examiner* — Keling Zhang
(74) *Attorney, Agent, or Firm* — Schwegman Lundberg & Woessner, P.A.

(57) ABSTRACT

Various aspects disclosed a catalyst particle for catalyzing the production of syngas from carbon dioxide and methane. The catalyst particle includes a metal oxide substrate. The substrate includes a particulate nickel phase. An exposed surface of the catalyst particle includes at least some of the particulate nickel phase. Additionally, the exposed surface is substantially nonporous.

16 Claims, 4 Drawing Sheets

(56) References Cited

U.S. PATENT DOCUMENTS

2018/0272322 A1    9/2018   Carr et al.
2018/0353942 A1   12/2018   Liang et al.

OTHER PUBLICATIONS

"International Application Serial No. PCT/US2022/038733, Invitation to Pay Additional Fees mailed Sep. 30, 2022", 2 pgs.

"International Application Serial No. PCT/US2022/038733, Written Opinion mailed Dec. 6, 2022", 7 pgs.

"International Application Serial No. PCT/US2022/038733, International Preliminary Report on Patentability mailed Feb. 8, 2024", 9 pgs.

"Canadian Application Serial No. 3,212,619, Office Action mailed Oct. 10, 2024", 4 pgs.

"U.S. Appl. No. 18/638,317, Restriction Requirement mailed Jul. 18, 2024", 8 pgs.

"U.S. Appl. No. 18/638,317, Response filed Sep. 12, 2024 to Restriction Requirement mailed Jul. 18, 2024", 7 pgs.

"U.S. Appl. No. 18/638,330, Restriction Requirement mailed Jul. 18, 2024", 7 pgs.

"U.S. Appl. No. 18/638,330, Response filed Sep. 12, 2024 to Restriction Requirement mailed Jul. 18, 2024", 7 pgs.

"U.S. Appl. No. 18/638,330, Non Final Office Action mailed Sep. 25, 2024", 10 pgs.

SYNGAS AND METHOD OF MAKING THE SAME

CROSS-REFERENCE TO RELATED APPLICATION

This application is a continuation of International Application No. PCT/US2022/038733, filed on Jul. 28, 2022, and published as WO 2023/009760 on Feb. 2, 2023, which claims the benefit of priority to U.S. Provisional Patent Application Ser. No. 63/203,784 entitled "SYNGAS AND METHOD OF MAKING THE SAME," filed Jul. 30, 2021, the benefit of priority of each of which is claimed herein, and which applications and publication are hereby incorporated herein by reference in their entirety.

BACKGROUND

Syngas, or synthesis gas, is a fuel gas mixture primarily including hydrogen, carbon monoxide, and often carbon dioxide. The name comes from its use as an intermediate in creating synthetic natural gas (SNG) and for producing ammonia or methanol.

SUMMARY OF THE INVENTION

Various aspects disclosed relate to a catalyst particle for catalyzing the production of syngas from carbon dioxide and methane. The catalyst particle includes a metal oxide substrate. The substrate includes a particulate nickel phase. An exposed surface of the catalyst particle includes at least some of the particulate nickel phase. Additionally, the exposed surface can be substantially nonporous.

Various aspects disclosed relate to a catalyst particle for catalyzing the production of syngas from carbon dioxide and methane. The catalyst particle can be a solid-solution catalyst particle formed from at least two solid reactants. The at least two solid reactants include atomic radii that are within about 15% of each other; substantially the same crystal structure; substantially the same electronegativity; substantially similar valency; or a combination thereof.

Various aspects disclosed relate to a method of making a catalyst particle for catalyzing the production of syngas from carbon dioxide and methane. The catalyst particle includes a metal oxide substrate. The substrate includes a particulate nickel phase. An exposed surface of the catalyst particle includes at least some of the particulate nickel phase. Additionally, the exposed surface can be substantially nonporous. The method includes mixing a nickel solution into a metal oxide powder to form mixed powder. The method further includes drying the mixed powder to form a dried paste. The method further includes crushing the dried paste to form a dried powder. The method further includes calcining the dried powder. The method further includes forming one or more particles from the dried powder. The method further includes calcining the particles to form the catalyst particle.

Various aspects disclosed provide a method of using a catalyst particle. The catalyst particle includes a metal oxide substrate. The substrate includes a particulate nickel phase. An exposed surface of the catalyst particle includes at least some of the particulate nickel phase. Additionally, the exposed surface can be substantially nonporous. The method includes contacting the catalyst particle with methane and carbon dioxide to produce carbon monoxide and hydrogen.

Various aspects disclosed provide a method of using syngas. The method includes using a catalyst particle to form the syngas. The catalyst particle includes a metal oxide substrate. The substrate includes a particulate nickel phase. An exposed surface of the catalyst particle includes at least some of the particulate nickel phase. Additionally, the exposed surface can be substantially nonporous. Forming syngas includes contacting the catalyst particle with methane and carbon dioxide to produce carbon monoxide and hydrogen of the syngas. The method of using the syngas includes forming a product from a feedstock comprising the syngas.

Various aspects disclosed provide a product comprising about 40 wt % to about 100 wt % carbon produced according to a method of using syngas. The method includes using a catalyst particle to form the syngas. The catalyst particle includes a metal oxide substrate. The substrate includes a particulate nickel phase. An exposed surface of the catalyst particle includes at least some of the particulate nickel phase. Additionally, the exposed surface can be substantially nonporous. Forming syngas includes contacting the catalyst particle with methane and carbon dioxide to produce carbon monoxide and hydrogen of the syngas. The method of using the syngas includes forming a product from a feedstock comprising the syngas.

Various aspects disclosed provide a reaction vessel. The reaction vessel includes a catalyst particle located within the reaction vessel. The catalyst particle includes a metal oxide substrate. The substrate includes a particulate nickel phase. An exposed surface of the catalyst particle includes at least some of the particulate nickel phase. Additionally, the exposed surface can be substantially nonporous.

The present disclosure presents numerous advantages and benefits, at least some of which are unexpected. For example, according to various aspects, the disclosed method of making syngas using the instant catalyst can produce a high yield of syngas. Additionally, according to various aspects, the disclosed catalyst particle can be capable of catalyzing the reaction to produce syngas without coking of the catalyst particle for a prolonged period of time. Additionally, according to various aspects, it was unexpectedly found that despite the catalyst particle having a reduced surface area compared to conventional catalysts that may have a higher degree of porosity, the instantly disclosed catalyst can be capable of producing a comparable of greater yield of syngas by surface area of the catalyst, by weight of the catalyst, by volume of the catalyst, or both, all while being substantially free of coke.

BRIEF DESCRIPTION OF THE FIGURES

The drawings illustrate generally, by way of example, but not by way of limitation, various aspects of the present invention.

DETAILED DESCRIPTION OF THE INVENTION

Figure 1:
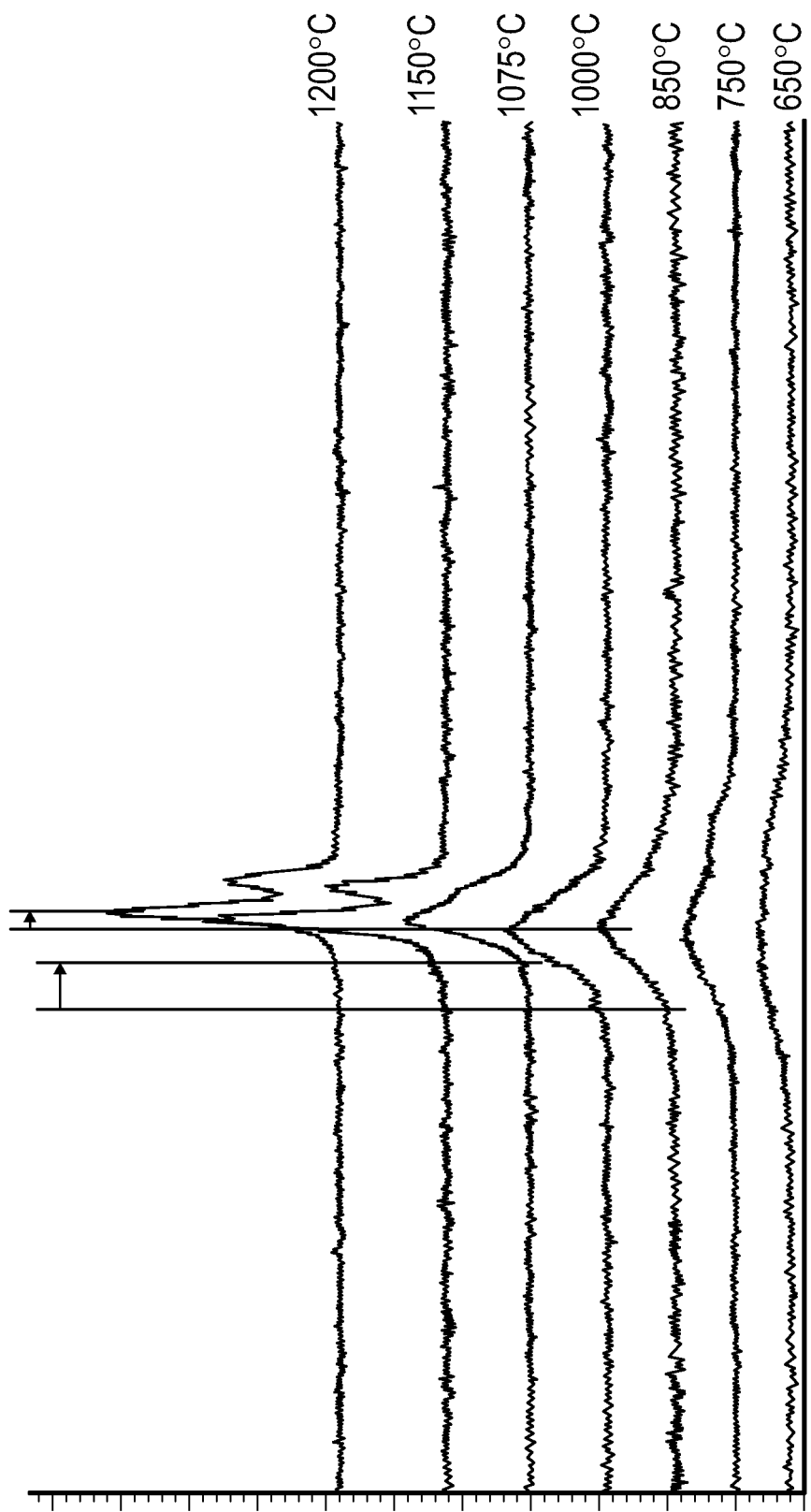
FIG. 1 is an X-Ray Diffraction plot, in accordance with various aspects.

Reference will now be made in detail to certain aspects of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range. The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that about 0 wt % to about 5 wt % of the composition is the material, or about 0 wt % to about 1 wt %, or about 5 wt % or less, or less than or equal to about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

Described herein is a catalyst particle (alternatively a catalyst, a solid-solution catalyst, or a solid-solution catalyst particle) and method for producing syngas using the catalyst particle. Syngas, or synthesis gas, is a gas mixture primarily of hydrogen, carbon monoxide, and possibly some carbon dioxide. Syngas can be a product of coal gasification and has been used for electricity generation. Syngas is combustible and can also be used as a fuel for internal combustion engines.

Syngas can be produced from many sources, including natural gas, coal, biomass, or virtually any hydrocarbon feedstock, by reaction with steam (e.g., steam reforming), carbon dioxide (e.g., dry reforming) or oxygen (e.g., partial oxidation). Syngas can be an intermediate resource for production of hydrogen, ammonia, methanol, and synthetic hydrocarbon fuels. It is also used as an intermediate in producing synthetic petroleum for use as a fuel or lubricant via the Fischer-Tropsch process.

The instant disclosure is drawn towards a dry reforming process for forming syngas. Dry reforming is a method of producing syngas from the reaction of carbon dioxide with hydrocarbons such as methane. Syngas is conventionally produced via a steam reforming reaction or coal gasification. However, in recent years, increased concerns relating to the contribution of greenhouse gases to global warming have increased interest in the replacement of steam as a key reactant with carbon dioxide as a replacement reactant for steam. Dry reforming offers an alternative to steam reforming. However, coking of the catalyst is a particular problem with conventional dry reforming techniques. As described further herein steam can be used during a dry reforming process to cleanse the catalyst. However, the coking problems associated with dry reformation processes have led people to use steam reforming processes despite the fact that the process as a whole tends to be less energy efficient than a dry reformation process. The instantly described dry reformation process, however, addresses the catalyst coking issues associated with convention dry reformation processes.

The dry reforming reaction may be represented as shown below:

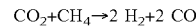
$$CO_2 + CH_4 \rightarrow 2\ H_2 + 2\ CO$$

Thus, two greenhouse gases (carbon dioxide and methane) are consumed and useful chemical building blocks (hydrogen and carbon monoxide) are produced. A challenge to the commercialization of this process is achieving a relevant yield of hydrogen and carbon monoxide.

The method according to the instant disclosure includes treating a catalyst particle with methane and carbon dioxide to produce carbon monoxide and hydrogen (syngas). The molar ratio of the methane to carbon dioxide supplied to the catalyst particle can be about 5:1 to 1:5 (mole:mole), about 2:1 to 1:2, or about 1:1. These ratios exclude the presence of any other gas present besides carbon dioxide and methane.

The catalyst particle that is used for the production of syngas from carbon dioxide and methane is a solid-solution catalyst particle. As understood, a solid solution refers to mixture of two solids that coexist as a new solid, or lattice that includes a degree of crystallinity while also including at least some amorphous character. As a non-limiting example, the amorphous portion of the solid-solution catalyst particle can be in range of from about 0.5 wt % to about 10 wt % of the solid-solution catalyst particle, about 2 wt % to about 7 wt %, about 3 wt % to about 5 wt %, less than, equal to, or greater than about 0.5 wt %, 1, 1.5, 2, 2.5, 3, 3.5, 4, 4.5, 5, 5.5, 6, 6.5, 7, 7.5, 8, 8.5, 9, 9.5, or about 10 wt %. The mixing can be accomplished by combining the two solids when they have been melted into liquids at high temperatures and then cooling the resulting product to form the new solid or by depositing vapors of the starting materials onto substrates to form thin films. As with liquids, solids have different degrees of mutual solubility, depending on their chemical properties and crystalline structure, which determine how their atoms fit together in the mixed crystal lattice. The mixed lattice may be substitutional, in which the atoms of one starting crystal replace those of the other, or interstitial, in which the atoms occupy positions normally vacant in the lattice. The substances may be soluble over a partial or even complete range of relative concentrations, producing a crystal whose properties vary continuously over the range.

The reactants that form the solid-solution catalyst particle can be chosen from reactants that are capable of forming a solid-solution such as at least two reactants having atomic radii that are within about 15% of each other; substantially the same crystal structure; substantially the same electronegativity; substantially similar valency; or a combination thereof. The reactants can generally be chosen from metal oxides and metal oxide precursors. In some specific examples, the catalyst particle can include a substantially nonporous metal oxide substrate and a particulate nickel phase dispersed about the metal oxide substrate and at least partially embedded therein. Examples of metal oxides for the substrate can include magnesium oxide (MgO), nickel oxide (NiO), iron oxide (FeO), cobalt oxide (CoO), manganese oxide (MnO), or a mixture thereof. The mixture can include any combination or sub-combination of the metal oxides. For example, the mixture can be a binary mixture, tertiary mixture, quaternary mixture, or the like. In any mixture, the concentration of each of the metal oxides can be substantially the same, alternatively, the concentration of at least one metal oxide can be different from the concentration of at least one different metal oxide.

The nonporous nature of the catalyst particle can be understood to refer to a "surface porosity" meaning that the catalyst particle can be free of pores that extend from the surface of the catalyst particle towards the interior of the catalyst particle. The nonporous nature of the catalyst particle can further be characterized by a lack of "internal porosity" meaning that the catalyst particle can be free of pores that extend through at least a portion of the catalyst particle. In some examples, the nonporous nature of the catalyst particle can refer to both the surface porosity and the internal porosity. Surface porosity, internal porosity, or both can be characterized by having a minimal number of pores or by individual pores, that may be present, having a small major dimension. A "major dimension" refers to the largest of the length, width, or thickness of an object. For example, any surface pores or through pores may have a width of less than nm, less than 40 nm, less than 30 nm, less than 20 nm, less than 10 nm, in a range of from about 10 nm to about 50 nm, about 10 nm to about 30 nm, or about 10 nm to about 15 nm. According to various aspects, a pore can account for less than about 20% of the total surface area of the catalyst particle, less than about 10% of the total surface area of the catalyst particle, less than about 5% of the total surface area of the catalyst particle, less than about 1% of the total surface area of the catalyst particle, or 0% of the total surface area of the catalyst particle.

The nonporous nature of the catalyst particle can help to prevent "coking" of the catalyst. Coking is one of several mechanisms that can be responsible for deactivation of a catalyst used for dry reformation of carbon dioxide. Coking refers to the deposition of coke (a hard, strong, porous material of high carbon content) on the catalyst. If the catalyst particle has porosity, the coke can penetrate the pores and prevent reactants from interacting with active sites on the catalyst particle. However, the instant catalyst particle can be nonporous and has a somewhat smooth-glassy surface, thus preventing or reducing coke from being deposited in any pores or on the surface of the catalyst particle.

Conventional catalyst particle design principles counsel against designing the catalyst particle to have such a low porosity. This is because it is thought that increasing porosity allows for a greater surface area to distribute active particles on and, therefore, produce more product. However, the inventors have surprisingly and unexpectedly found that the instant catalyst particle can be capable of providing a very high yield of syngas despite having a comparatively smaller active surface area (e.g., exposed nickel phase) than a comparative catalyst particle having a higher degree of porosity. Although the instant catalyst particle does not have an increased surface area resulting from porosity, in some examples the surface area of the catalyst particle can be increased by including a series of surface structures such as grooves, undulations, or peak-and-valleys on the surface of the catalyst particle. Unlike pores, which can be characterized as penetrating the surface of the catalyst particle, the surface structures do not penetrate the surface of the catalyst particle. For example, a bottom or lowest portion of the surface structure is still characterized as the surface of the catalyst particle.

The metal oxide substrate can be generally a continuous structure. The metal oxide substrate gives the catalyst particle its overall structure. The overall structure of the catalyst particle can be substantially spherical, substantially cylindrical, substantially flat, or it can have an undulating profile. The catalyst particle can be solid. Alternatively, the catalyst particle can have at least one through pore. For example, the catalyst particle can have a "wagon wheel" structure in which the catalyst particle is circular with a number of through pores extending from a first end of the catalyst particle to a second end of the catalyst particle. The catalyst particle can have any number of through pores, for example the catalyst particle can have a single through pore or a plurality of through pores. Including the through pores can have the benefit of increasing the surface area of the catalyst particle (relative to a corresponding catalyst particle that is free of a through pore or has fewer through pores), thus potentially allowing for more syngas production. In some examples, it is possible for the catalyst particle to include a number of indentations that penetrate partially through the thickness of the catalyst particle this can be helpful to increase the surface area as well. The through pore(s) can extend substantially along a largest dimension of the catalyst particle or a smaller dimension. A largest dimension of the catalyst particle can be in a range of about 1 to about 20 mm, about 1 mm to about 10 mm, in a range of about 4 mm to about 6 mm, or less than, equal to, or greater than about 1 mm, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or about 20 mm. The largest dimension can refer to a length, width, or diameter of the catalyst particle.

The particulate nickel phase of the catalyst particle can include elemental nickel, nickel oxide, or a mixture thereof. In total, the particulate nickel phase can be about 0.2 wt % to about 30 wt % of the catalyst particle, about 14 wt % to about 25 wt % of the catalyst particle, or less than, equal to, or greater than about 0.2 wt % of the catalyst particle, 1, 2, 3, 4, 5, 6, 7, 8, 9, 10, 11, 12, 13, 14, 15, 16, 17, 18, 19, 20, 21, 22, 23, 24, 25, 26, 27, 28, 29, or about 30 wt % of the catalyst particle. The particulate nickel phase can be homogenously or heterogeneously distributed about the metal oxide substrate. In examples where the particulate nickel phase can be heterogeneously distributed about the metal oxide substrate, a major portion (e.g., greater than 50 wt %) of the particulate nickel phase can be located proximate to a surface of the metal oxide substrate. In most examples, the particulate nickel phase includes nickel oxide as opposed to elemental nickel.

At least a portion of the particulate nickel phase can be exposed on a surface of the metal oxide substrate. The portion of the particulate nickel phase that can be exposed on the surface of the metal oxide substrate is available to be contacted directly with the reactants and catalyze the reaction to produce syngas. The exposed portion of the particulate nickel phase is bound to the metal oxide substrate. Thus, the exposed portion of the particulate nickel phase can be free of unbound or free nickel or nickel oxide.

The nickel of the particulate nickel phase that is exposed on a surface of the metal oxide substrate can be primarily nickel oxide as opposed to elemental nickel. For example, the nickel of the particulate nickel phase that is exposed on a surface of the metal oxide substrate can be from about 80 wt % to about 100 wt % nickel oxide, about 95 wt % to about 100 wt % nickel oxide, less than, equal to, or greater than about 80 wt %, 85, 90, 95, or 100 wt % nickel oxide. In total, the amount of the particulate nickel phase exposed on a surface of the metal oxide substrate can be in a range of from about 10 wt % to about 30 wt % of the particulate nickel phase, about 14 wt % to about 18 wt % of the particulate nickel phase, less than, equal to, or greater than about 10 wt %, 11, 12, 13, 14, 15, 16, 17, 18, 19, 20, 21, 22, 23, 24, 25, 26, 27, 28, 29, or 30 wt %. The exposed particulate nickel phase can account for about 10% to about 90% of the total surface area of the catalyst particle, about 20% to about 80% of the total surface area of the catalyst particle, about 30% to about 70% of the total surface area of the catalyst particle, about 40% to about 60% of the total surface area of the catalyst particle, less than, equal to, or greater than about 10% of the total surface area of the catalyst particle, 15, 20, 25, 30, 35, 40, 45, 50, 55, 60, 65, 70, 75, 80, 85, or about 90% of the total surface area of the catalyst particle.

As described herein, the particulate nickel phase can be generally free of unbound or free elemental nickel. However, to mitigate the risk of free elemental nickel being present, the catalyst can include potassium ions distributed in or at the surface of the catalyst particle. Where present, the potassium ions range from about 0.2 wt % to about 5 wt % of the catalyst particle, about 1 wt % to about 2 wt % of the catalyst particle, less than, equal to, or greater than about 0.2 wt % of the catalyst particle, 0.5, 1, 1.5, 2, 2.5, 3, 3.5, 4, 4.5, or about 5 wt % of the catalyst particle. The potassium ions can be supplied as potassium nitrate, potassium acetate, potassium carbonate, or a mixture thereof. In various aspects, the catalyst particle is free of free elemental nickel. However, if free elemental nickel is present, it is expected to be less than about 2 wt % free elemental nickel in the particulate nickel phase, less than about 0.5 wt % free elemental nickel in the particulate nickel phase, or free of free elemental nickel in the particulate nickel phase.

In use, the catalyst particle can be contacted with a feed stream including methane and carbon dioxide to produce carbon monoxide and hydrogen (syngas). To help increase the coverage of the catalyst particle, the steam and/or another gas (e.g., an inert gas such as argon) can be contacted with the catalyst particle continuously or intermediately at any suitable rate such as a slow trickle. The catalyst can be able to produce syngas from a wide array of methane and carbon dioxide sources. For example, the methane and carbon dioxide source can be a feed stream of industrial waste (e.g., a power plant exhaust source, fermentation byproduct or primary product gas, landfill methane reclamation, bio-digestor methane production, steel furnace exhaust gas, ammonia byproducts, methanol tailgas, flare gas, or the like) an air captured carbon source, or a mixture thereof. In some examples, the feed stream can be captured and supplied to the solid-solution catalyst particle. In some other examples, the source of the feed stream can be directly coupled (e.g., co-located) with an apparatus for the production of syngas, such that the feed stream is directly put into contact with the solid-solution catalyst particle. Thus, a producer of an environmentally unfriendly gas can recoup environmental, economic, and/or social benefits from an off gas use. According to various examples, the feed stream can include from about 20% wt % to about 99 wt % carbon dioxide, about 30 wt % to about 99 wt % carbon dioxide, about 40 wt % to about 80 wt % carbon dioxide, about 40 wt % to about 60 wt % carbon dioxide, less than, equal to, or greater than, about 20 wt % carbon dioxide, 25, 30, 35, 40, 45, 50, 55, 60, 65, 70, 75, 80, 85, 90, 95, or about 99 wt % carbon dioxide. The feed stream can alternatively, include from about 20% wt % to about 99 wt % methane, about 30 wt % to about 99 wt % methane, about 40 wt % to about 80 wt % methane, about 40 wt % to about 60 wt % methane, less than, equal to, or greater than, about 20 wt % methane, 25, 30, 35, 40, 45, 50, 55, 60, 65, 70, 75, 85, 90, 95, or about 99 wt % methane.

In general, pollutants such as sulfur do not negatively impact the performance of the catalyst particle. Within the methane and carbon dioxide source, the methane and carbon dioxide can be at a molar ratio of about 5:1 to about 1:5, about 2:1 to about 1:2, or about 1:1. These ratios exclude the presence of any other gas present besides carbon dioxide and methane.

Before the catalyst particle is contacted with the feed stream including carbon dioxide and methane, the catalyst particle can be activated. Activating the catalyst particle can include contacting the catalyst particle with a mixture of hydrogen gas and nitrogen gas for a time in a range of from about 0.1 hour to about 6 hours, about 2 hours to about 5 hours, less than, equal to, or greater than about 0.11 hour, 0.5, 1, 2, 3, 4, 5, or 6 hours. Activation can occur at a temperature in a range of from about 400° C. to about 600° C., about 450° C. to about 500° C., less than, equal to, or greater than about 400° C., 410, 420, 430, 440, 450, 500, 550, or about 600° C. A ratio of hydrogen gas to nitrogen gas used to activate the catalyst particle can be in a range of from about 90:10 to about 70:30 or about 85:15 to about 75:25.

The carbon monoxide and hydrogen of the syngas can be produced in a molar ratio of about 3:1, 2:1, 1:1, 1:2, or about 1:3. These ratios exclude the presence of any other gas present besides carbon monoxide and hydrogen. In the reaction at least 70 wt % of the carbon dioxide and methane that contacts the catalyst particle are converted to carbon monoxide and hydrogen per turn, at least 90 wt % of the carbon dioxide and methane that interact with the catalyst particle are converted to carbon monoxide and hydrogen per turn, about wt % to about 99 wt %, about 90 wt % to about 99 wt %, or about 95 wt % to about 98 wt %. Thus, the catalyst particle of the instant disclosure can be capable of producing commercially viable yields of syngas. In addition to the yield, the kinetics of the catalyst particle are very fast. For example, the catalyst particle can have a turnover frequency of about 2000 to about 7000, about 3000 to about 5000, less than, equal to, or greater than about 2000, 2500, 3000, 3500, 4000, 4500, or 5000. As understood a "turn" refers to a contacting event of the carbon dioxide and methane with the catalyst particle to form syngas. A "turnover frequency" quantifies the specific activity of a catalyst particle for a designated reaction under defined reaction conditions by the number of molecular reactions or catalytic cycles occurring as a unit of turns per hour.

The kinetics and yield of the reaction can be impacted by the pressure at which the methane and carbon dioxide are contacted with the catalyst particle. For example, methane and carbon dioxide can be contacted with the catalyst particle at a pressure in a range of from about 25 KPa to about 2500 KPa, about 30 KPa to about 2100 KPa, less than equal to or greater than about KPa, 50, 100, 150, 200, 250, 300, 350, 400, 450, 500, 550, 600, 650, 700, 750, 800, 850, 900, 950, 1000, 1500, 2000, or about 2500 KPa.

The kinetics and yield of the reaction can also be impacted by the flow rate of the feed stream. In some examples the flow rate of the feed stream can be measured in terms of a gas hourly space velocity (GHSV) that can be in a range of from about 500 $h^{-1}$ to about 11000 $h^{-1}$ about 1000 $h^{-1}$ to about 10000 $h^{-1}$, less than, equal to, or greater than about 500 $h^{-1}$, 1000, 1500, 2000, 25000, 3000, 3500, 4000, 4500, 5000, 5500, 6000, 6500, 7000, 7500, 8000, 8500, 9000, 9500, 10000, 10500, or 11000 $h^{-1}$.

Additionally, the kinetics and yield of the reaction can be impacted by the temperature at which the reaction is performed. In some examples, the reaction can be performed at a temperature in a range of from about 530° C. to about 1100° C., about 800° C. to about 990° C., less than, equal to, or greater than about 530° C., 540, 550, 560, 570, 580, 590, 600, 610, 620, 630, 640, 650, 660, 670, 680, 690, 700, 710, 720, 730, 740, 750, 780, 790, 800, 810, 820, 830, 840, 850, 860, 870, 880, 890, 900, 910, 920, 930, 940, 950, 960, 970, 980, 990, 1000, or 1100° C. In some examples, the temperature will be provided from the feed stream. Additionally, or in other examples the catalyst particle may be located in a vessel, which can be heated to a certain temperature to achieve the desired reaction temperature.

Importantly, and contrary to conventional catalysts for the production of syngas, the instantly disclosed catalyst particle can be substantially free of coking during performance of the method. For example, the catalyst particle can be free of coking for a period of time of at least 1 week, at least one month, at least 6 months, at least 1 year, at least 2, years or at least 3 years. By "free of coking" it is meant that the catalyst particle can continuously catalyze the syngas production reaction without about 20% to about 100% loss of catalytic activity, about 40% to about 80% loss of catalytic activity, less than, equal to, or greater than about 30% loss of catalytic activity, 35, 40, 45, 50, 55, 65, 70, 75, 80, 85, 90, 95, or about 100% loss of catalytic activity.

Although the catalyst particle of the instant disclosure shows good anti-coking properties, the catalyst particle can be steam treated, if desired, to remove any amount of coke that may be present. To steam treat the catalyst particle, the flow of the feed stream is cut off, and steam at a temperature in a range of from about 150° C. to about 300° C., about 200° C. to about 260° C., or less than, equal to, or greater than about 150° C., 160, 165, 170, 175, 180, 185, 190, 195, 200, 205, 210, 215, 220, 225, 230, 235, 240, 245, 250, 255, 260, 265, 270, 275, 280, 285, 290, 295, or about 300° C., is fed to the catalyst particle. Steam can be fed to the catalyst particle for a suitable amount of time, such as an amount of time in a range of from about 1 hour to about 20 hours, about 2 hours to about 15 hours, less than, equal to, or greater than about 1 hour, 2, 3, 4, 5, 6, 7, 8, 9, 10, 11, 12, 13, 14, 15, 16, 17, 18, 19, or about 20 hours. The performance of the catalyst can be continually monitored and if the performance drops below a certain threshold the syngas production can be stopped and the catalyst can be steam treated to remove any coke that may be present.

The catalyst particles described herein can be formed according to any suitable method. An example of a suitable method can include mixing a nickel solution into a metal oxide powder to form a mixed powder. Alternatively, the mixed powder can be formed by co-precipitation of a nickel solution and a single metal or multiple metals solution selected from the group of cobalt, iron, manganese and magnesium. The nickel solution can include nickel(II) nitrate hexahydrate, nickel(II)di-acetate, nickel(II)carbonate, or a combination thereof. In some examples, nickel(II) nitrate hexahydrate can be particularly suited for the method. The metal oxide powder can include any of the metal oxides described herein. In some examples, magnesium oxide can be particularly well suited to form a solid-solution catalyst along with nickel(II) hexahydrate. In some examples, it was found that controlling the $d_{50}$ of the metal oxide particles present helped to form the solid-solution catalyst. For example, suitable $d_{50}$ values for the metal oxide can be in a range of from about 2 µm to about 120 µm, about 5 µm to about 100 µm, less than, equal to, or greater than about 2 µm, 5, 10, 15, 20, 25, 30, 35, 40, 45, 50, 55, 60, 65, 70, 75, 80, 85, 90, 100, 105, 110, 115, or about 120 µm. The nickel solution and the metal oxide are readily soluble in each other, which facilitates even mixing.

After the mixed powder is formed, the mixed powder can be dried. The mixed powder can be air dried or heated. Following drying, the mixed powder becomes a dried paste. The dried paste can be then crushed to form a dried powder. Crushing can be accomplished using ball-milling, granulation, or a combination thereof. Crushing can occur for a range of time of about 0.5 hours to about 5 hours, about 2 hours to about 4 hours, less than, equal to, or greater than about 0.5 hours, 1 hour, 2 hours, 3 hours, 4 hours, or 5 hours.

The dried powder can then be calcined. Calcining the dried powder converts the nickel solution to nickel oxide. Calcining can occur at a temperature in a range of from about 400° C. to about 2000° C., about 500° C. to about 1500° C., about 950° C. to about 1050° C., less than, equal to, or greater than about 400° C., 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or about 2000° C. A temperature of 950° C. to about 1050° C. has been found to be particularly effective. Calcining can occur for a time in a range of from about 0.5 hours to about 4 hours, about 1 hour to about 3 hours, less than, equal to, or greater than about 0.5 hours, 1, 1.5, 2, 2.5, 3, 3.5, or 4 hours.

One or more particles are formed from the dried powder. The particles are formed as individual particles that have dimensions that are substantially similar to the final catalyst particle. Those particles are calcined to form the catalyst particle. Calcining of the particles can be performed at a temperature in a range of from about 800° C. to about 1500° C., about 900° C. to about 1100° C., less than, equal to, or greater than about 800° C., 850, 900, 950, 1000, or 1500° C. Calcining can occur for a time in a range of from about 0.5 hours to about 48 hours, about 0.5 hours to about 30 hours, about 0.5 hours to about 24 hours, about 0.5 hours to about 20 hours, about 0.5 hours to about 10 hours, about 0.5 hours to about 4 hours, about 1 hour to about 3 hours, less than, equal to, or greater than about 0.5 hours, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, or about 48 hours. At any point during the method, potassium nitrate can be added to a mixture, powder or paste.

The catalyst particle has been described as a solid particle. However it is also possible and within the scope of the instant disclosure for the material of the catalyst particle to be a coating present on a substrate that is substantially inert to methane, carbon dioxide, carbon monoxide, and hydrogen. Examples of such a substrate include a silica or a ceramic. The substrate can take on any suitable shape such as a sphere, a rod, a latticed structure, a porous structure, or the like. The average thickness of the coating can be in a range of from about 0.1 mm to about 2.5 mm, about 0.15 mm to about 2 mm, less than, equal to, or greater than about 0.1 mm, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, or about 2.5 mm. The substrate can be coated with the catalyst to any suitable degree. For example, about 30% to about 100% of the total surface area of the substrate can be coated with the catalyst, about 40% to about 90% of the total surface area of the substrate can be coated with the catalyst, about 50% to about 80% of the total surface area of the substrate can be coated with the catalyst, less than, equal to, or greater than about 30% of the total surface area of the substrate, 35, 40, 45, 55, 60, 65, 70, 75, 80, 85, 90, 95, or about 100% of the total surface area of the substrate. Manufacturing the catalyst coated substrate can largely follow the protocols describe herein above with the additionally step of applying the mixed powder to the substrate material and drying the mixed powder thereon ahead of calcining the dried powder to form the catalyst coating on the substrate.

To produce syngas at a commercially desirable level, the catalyst particle can be incorporated into an assembly. For example, the catalyst particle can be located within a reaction vessel. According to various examples, a reaction vessel can include a tube. The tube can be configured to have a generally cylindrical profile with an inlet and an outlet. Without being so limited, the inlet can be located proximate to or at the bottom of the tube and the outlet can be located proximate to or at the top of the tube.

The reaction vessel can take on other shapes and configurations as well. For example, in some cases a heat source such as a furnace can be placed in thermal communication with the reaction vessel. The reaction vessel can include a feedback loop to direct carbon dioxide produced by the heat source to the reaction vessel to participate in the instantly described method for producing syngas. Routing carbon dioxide back to the reaction vessel can significantly reduce the carbon dioxide emissions of a plant using the instantly disclosed method. In some examples, the carbon dioxide emissions can be non-existent.

The catalyst particle can be fixed within the reaction vessel. For example, the catalyst particle can be adhered to an inner surface of the reaction vessel. As another example, a retention device can be located within the reaction vessel and the catalyst particle can be retained by the retention device. The reaction assembly can include any plural number of catalyst particles. The optimum number of catalysts particles in the reaction assembly can be determined with a loading test. This can involve checking for void space in the and packing density in the assembly to optimize the amount of catalyst particles. The composition (e.g., chemical composition) or physical characteristics (e.g., catalyst particle size) of the individual catalyst particles can be the same or different. The distribution of the catalyst particles can be an even distribution (e.g., an equal amount of catalyst particles across the reaction vessel) or an uneven distribution (e.g., a gradient of amounts of catalyst particles or a large or small concentration of catalyst particles at a first location relative to a second location). An even distribution of the catalyst particles can be helpful to increase the possibility that as much feed gas as possible can contact the catalyst particles. If the catalyst particles are only placed at one location, for example, there can be a risk that some feed gas may go past the catalyst particles without reacting, thereby decreasing the yield of syngas relative to the amount of feed gas supplied.

The metal of the reaction vessel can be a metal showing high thermal resistivity as well as inertness to the feed gas and syngas. The high thermal resistivity can be helpful to maintain the integrity of the reaction vessel when exposed to the potentially high temperatures of the feed gas, the source of heat required to bring conditions inside the reaction vessel to a temperature suitable for conducting the reaction, as described herein, or both.

The syngas produced according to the instantly described methods can be used in many different industrial applications. For example, the syngas produced can be utilized as a feedstock that can be used to form a carbon containing substance such a paraffinic base oil, a paraffinic wax, a solvent, a fuel, ammonia, methanol, ethanol, propanol, butanol, pentanol, acetic acid, dimethoxyethane, or a mixture thereof.

Additional hydrogen can be formed from the carbon monoxide in the syngas. The additional hydrogen can be formed, for example, through what is called the water-gas-shift reaction represented below:

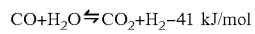

$$CO + H_2O \leftrightarrows CO_2 + H_2 - 41 \text{ kJ/mol}$$

The carbon monoxide used for the hydrogen synthesis can be provided from the syngas. In the process carbon monoxide can be used as a reductor to shift syngas entirely to $H_2$ (and $CO_2$). The high temperature water gas shift uses iron oxide as a catalyst and proceeds at a temperature in a range of from about 300° C. to about 500° C. A low-temperature process (e.g., around 200° C.) based on a copper-zinc oxide catalyst can drive the equilibrium further towards hydrogen, but requires clean feed gas. Thus, the hydrogen that can be produced by forming syngas can be increased through these reactions.

Additionally, any hydrogen gas or carbon monoxide gas can be purified. For example, the hydrogen gas or carbon monoxide gas can be purified using a pressure adsorption unit. This can produce hydrogen gas and carbon monoxide gas that can each have a purity of 90% to 99.9%.

Methanol can be another product that can be formed from syngas produced according to the instant disclosure. Methanol can be a desirable product because it is a versatile intermediate for the chemical industry, but can also serve as a fuel. Dimethyl ether (a derivative of methanol) can also be made from syngas and can be applicable as bottle gas for cooking (e.g., camping gas) or as a substitute for diesel fuel. Methanol is also used in the transesterification of vegetable oils to produce biodiesel. Methanol can be produced catalytically.

Examples of reactions used to produce methanol from syngas include the following reactions:

$$CO_2 + 3 H_2 \leftrightarrows CH_3OH + H_2O - 47 \text{ kJ/mol}$$

The above reaction can also be combined with the water-gas shift reaction described above, as shown below:

$$CO + 2 H_2 \rightleftharpoons CH_3OH - 91 \text{ kJ/mol}$$

In examples where the syngas can be used to produce ethanol, carbon dioxide can be present in the mixture of products. Specifically, the carbon dioxide can be present in an amount as high as 50 wt % (or as high as 30 wt %, 35 wt %, 40 wt % or 45 wt %) of the total amount of products. The carbon dioxide can be captured and used as a reactant for syngas production. The exact amount carbon dioxide can depend on whether it is a non-converted by-product, or the final carbon content of a produced product.

Additionally, hydrocarbons used to form the basis of gasoline, diesel, jet fuel, and chemicals such as olefins and waxes can be synthesized using the syngas produced according to the instant disclosure. The hydrocarbons can be formed using Fischer-Tropsch Synthesis (FTS). FTS can be used in gas-to-liquids (GTL) and coal-to-liquids (CTL) plants. The product distribution resulting from an FTS process can include more than liquids and hydrocarbons alone, and can include methane and alkanes, as well as hydrocarbons having the formula $C_nH_{2n+2}$ (with n is in a range of from 1 to 100), alkenes or olefins (having the formula $C_nH_{2n}$ where n is greater than or equal to 2), and to a lesser extent oxygenated products such as alcohols. Catalysts for the Fischer-Tropsch Synthesis include those based on cobalt or iron. According to various aspects, the iron-based catalyst can be an iron carbide under reaction conditions, whereas cobalt works in the metallic state. Reaction conditions include temperatures in a range of from about 200° C. to 350° C. and pressures in a range of from about 20 and 50 bar.

Whichever product is formed from the syngas according to the instant disclosure, the product can include a high amount (by wt %) of carbon that is produced from the syngas. For example, a product formed using the syngas according to the instant disclosure can be in a range of from about 40 wt % to about 100 wt % carbon produced from the syngas of the instant disclosure, about 50 wt % to about 100 wt %, about 70 wt % to about 100 wt %, less than, equal to, or greater than about 40 wt %, 41, 42, 43, 44, 45, 46, 47, 48, 49, 50, 51, 52, 53, 54, 55, 56, 57, 58, 59, 60, 61, 62, 63, 64, 65, 66, 67, 68, 69, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 wt %.

In some examples, a high degree of the carbon produced by the instantly described methods of making syngas can be originated from a source of carbon dioxide emissions. For example, about 40 wt % to about 80 wt % of the carbon produced can be from a source of carbon dioxide emission (e.g., a co-product or by-product), or about 70 wt % to about 80 wt % of the carbon produced can be from a source of carbon dioxide emission, less than, equal to, or greater than about 40 wt %, 45, 50, 55, 60, 65, 70, 75, or about 80 wt %.

In some additional examples an even higher amount of the carbon produced in manufacturing syngas can be obtained. For example, if the carbon dioxide used to make syngas is combined with a biogas for the source of methane, it is possible for about 90 wt % to about 100 wt % of carbon to be produced from greenhouse gas emissions and or renewable sources, 95 wt % to about 100 wt %, less than, equal to, or greater than about 90 wt %, 91, 92, 93, 94, 96, 97, 98, 99, or about 100 wt %.

Additionally, because the syngas can be produced by a method that consumes greenhouse gases such as carbon dioxide and methane, a product formed from the syngas can have a low carbon score, can be carbon neutral, or have a carbon negative score. The carbon score can be determined by quantifying the amount of greenhouse gas that is removed from the atmosphere while making the product. For example, a carbon neutral product refers to a product that has a manufacturing process resulting in the net effect not adding greenhouse gases to the atmosphere. As a further example, a carbon negative product refers to a product that has a manufacturing process that results in a net effect of removing greenhouse gases from the atmosphere.

In some further examples the syngas process described herein can be useful to economically produce blue hydrogen. Blue hydrogen is understood to refer to hydrogen formed when a natural gas is split into hydrogen and carbon dioxide and where the carbon dioxide is captured and not released to the atmosphere. Conventional blue hydrogen production can be environmentally and/or economically undesirable because of the carbon dioxide that is formed owing to the emission of the carbon dioxide to the atmosphere or the requirements of storing the carbon dioxide so that it is not emitted into the atmosphere. However, using the syngas production method described herein, carbon dioxide produced to form blue hydrogen can be fed into the syngas production method as a feedstock to react with methane to form syngas.

In some further examples, a plant or device associated with producing the instantly disclosed syngas can be co-located with a plant or device for making any product that uses or can use syngas as an at least partially feedstock. That is syngas produced can be directly fed into a process for making a product.

EXAMPLES

Various aspects of the present invention can be better understood by reference to the following Examples which are offered by way of illustration. The present invention is not limited to the Examples given herein.

Example 1—Catalyst Preparation

Magnesium Oxide (MgO) powder was obtained and the loss on ignition (LOI) and water pickup of the MgO powder was determined. LOI was less than 5% and water pickup ranged from 10% to 75%. An amount of nickel nitrate hexa-hydrate ("NNHH") needed to reach about 15 wt % nickel based on the total dry weight of the MgO powder was added. The NNHH was then impregnated, according to an incipient wetness (IW) technique, into the MgO powder to form an impregnated powder. The impregnated powder was dried at a temperature in a range of from 90° C. to 100° C. in a rotary evaporator (rotavap) until a dry free flowing material was obtained. The obtained powder was calcined in air at 600° C. for 2 hrs. An acceptable aid (e.g., an organic lubricant such as Abril 1071 (a lubricant available from abril industrial waxes limited) was added to the obtained powder to produce a suitable amount of particles (each being about 2.5±0.5 mm diameter, and length such that an aspect ratio about is 1:1). The particles were calcined at 1000° C. for 2 hrs to obtain the catalyst.

Example 2—Catalyst Structure

The solid-solution state of the catalyst formed according to Example 1 was confirmed using X-Ray Diffraction (XRD), results are shown in FIG. 1. Formation of the Ni/Mg solid solution phase was detected at about 94 degrees (2-theta)(2θ) in the X-Ray diffractogram (spectra) of the catalyst. Crystallinity (ordered patterns of individual atoms) of the catalyst increased with increased calcination temperature (from 600° C. to 1,200° C.) which led to progressive sharpening of the peak. The catalyst was attained through a mixture of predominantly crystalline phase, but a minor amount of amorphous phase was also needed to retain external surface area for catalytic activity. A 100% crystalline material, as exemplified by the XRD spectra was obtained at 1,150° C. and 1,200° C. calcination, has zero surface area and exhibit very little catalytic activity. The formation of the "satellite peak" at the aforementioned two temperatures was a result of the highly crystalline reflective planes within the solid solution.

The data set showed that the optimal solid solution phase was produced by calcination between 1,000° C. and 1,075° C. representing a mixture of crystalline and amorphous solid solution.

Figure 2:
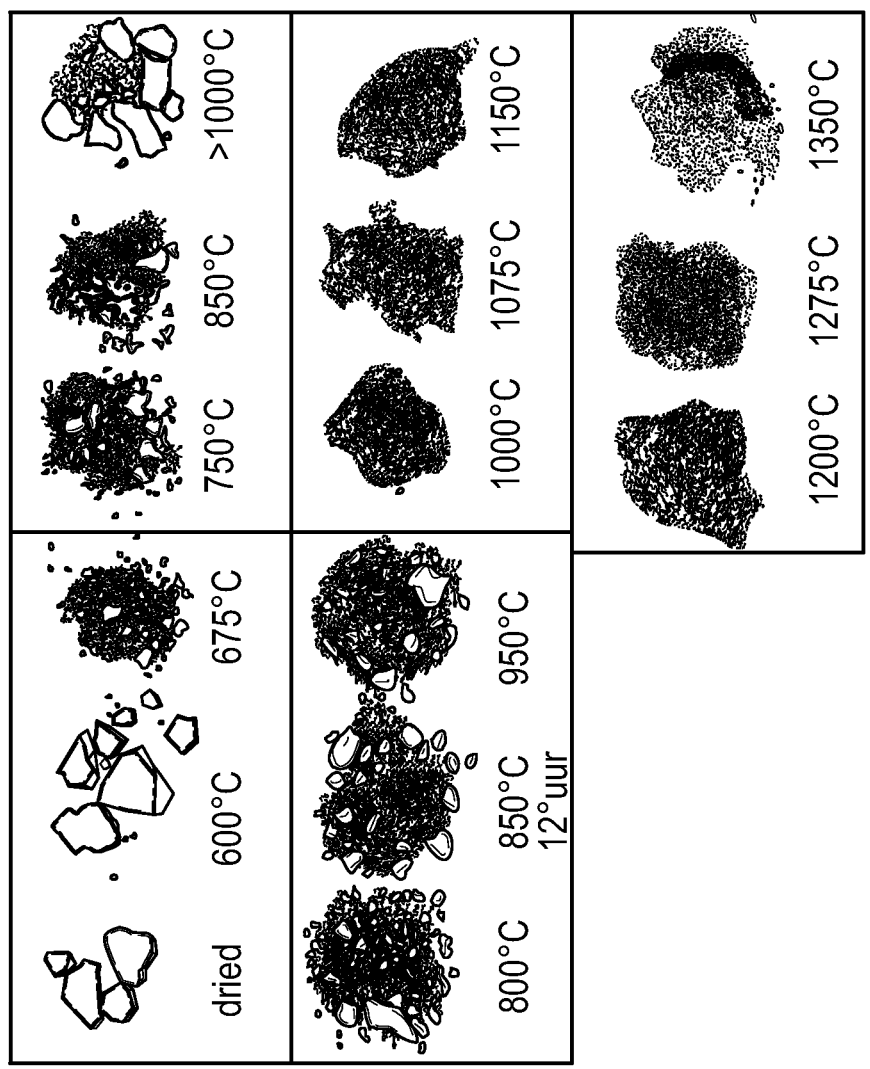
FIG. 2 provides a series of photographs showing catalyst particles calcined at different temperatures, in accordance with various aspects.

In addition to the XRD data, the series of images provided as FIG. 2 shows the progression of color of the samples towards the desired "olive green" color needed for optimal solid solution. The more intense the green, the more crystalline the material is. As shown in FIG. 2, calcination at 1,150° C. and above rendered the most intense green, indicating 100% crystallinity of the solid solution at virtually zero surface area.

Example 3—Catalyst Surface Area

Catalyst surface area, determined according to the Braunauer-Emmett-Teller (BET) theory, was determined as a function of the calcination temperature described herein above in Example 1. Results are shown in Table 1:

TABLE 1

| Calcination Temperature (° C.) | BET Surface Area (m²/g) |
|---|---|
| 850 | 26 |
| 1000 | 9 |
| 1150 | Less than 1 |

Example 4—Size of MgO Particles

The size of the MgO particles used in Example 1 was controlled in some aspects. The size was controlled by milling a quantity of MgO particles for about 6 hours in a Netzsch ball mill. This procedure resulted in the particle size distribution shown below in Table 2.

TABLE 2

| $d_{10}$ | 0.238 microns (μm) |
|---|---|
| $d_{50}$ | 0.430 microns (μm) |
| $d_{90}$ | 0.791 microns (μm) |
| $d_{99}$ | 1.400 microns (μm) |

Example 5—Syngas Production

Figure 3:
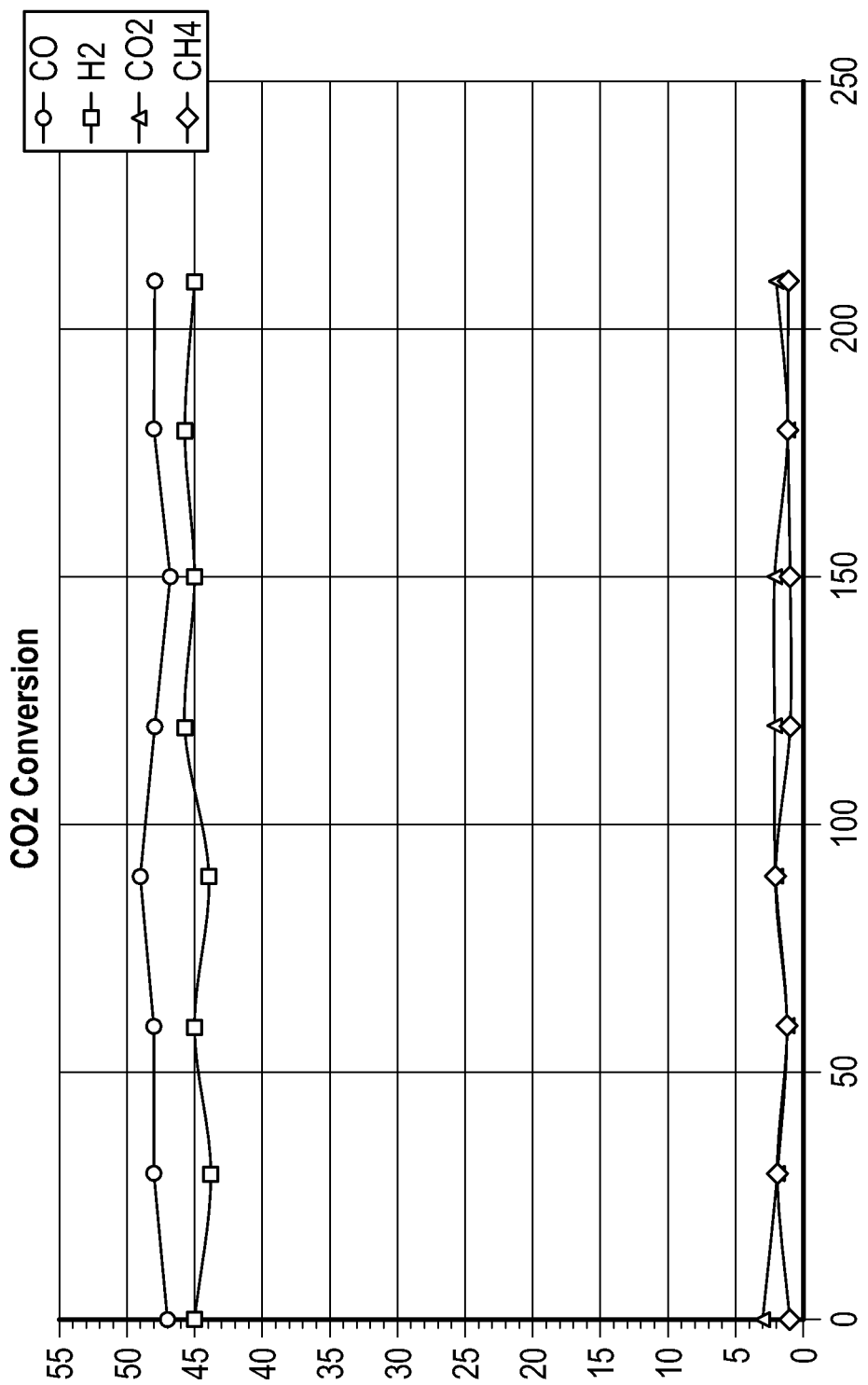
FIG. 3 is a graph showing the vol % of syngas constituents (x-axis) over time in hours (y-axis).

A catalyst was produced according to the protocol of Example 1. The catalyst was exposed to a feed gas that included 50 vol % methane and 50% carbon dioxide. The temperature of the feed gas was maintained at 800° C. and delivered at a GHSV of 10,000 h⁻¹. The pressure of the environment where the feed gas is contacted with the catalyst is maintained at 25 PSIG. The results are shown in FIG. 3. FIG. 3 is a graph showing the vol % of syngas constituents (x-axis) over time in hours (y-axis). As shown in FIG. 3, the syngas produced maintained a high amount of carbon monoxide and hydrogen for more than 200 hours. The constant production of hydrogen and carbon monoxide also showed that the catalyst was free of coking.

Example 6—Syngas Production

Figure 4:
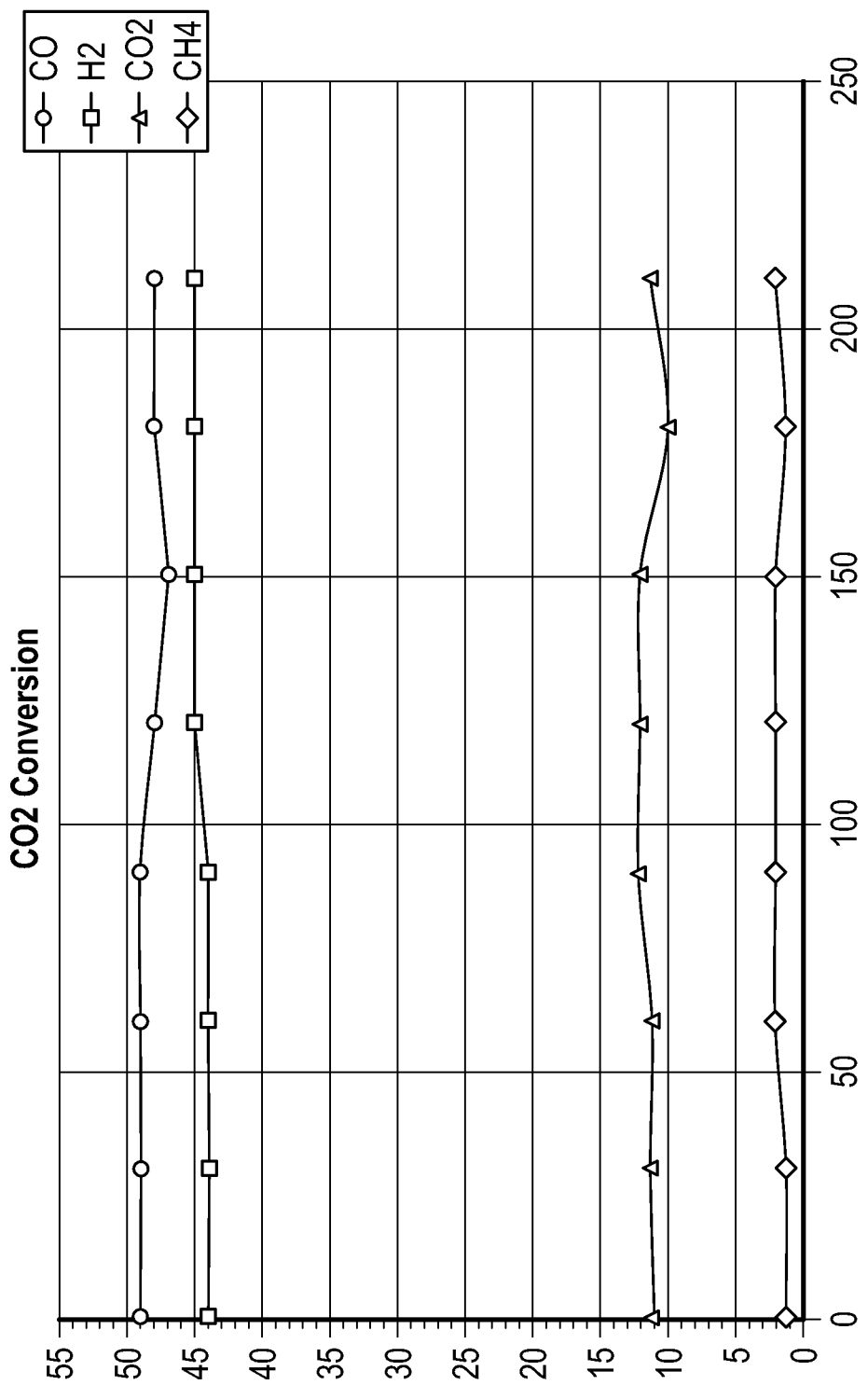
FIG. 4 is a graph showing the vol % of syngas constituents (x-axis) over time in hours (y-axis).

A catalyst was produced according to the protocol of Example 1. The catalyst was exposed to a feed gas that included 40 vol % methane and 60% carbon dioxide. The temperature of the feed gas was maintained at 800° C. and delivered at a GHSV of 10,000 h⁻¹. The pressure of the environment where the feed gas is contacted with the catalyst is maintained at 25 PSIG. The results are shown in FIG. 4. FIG. 4 is a graph showing the vol % of syngas constituents (x-axis) over time in hours (y-axis). As shown in FIG. 4, the syngas produced maintained a high amount of carbon monoxide and hydrogen for more than 200 hours. The constant production of hydrogen and carbon monoxide also showed that the catalyst was free of coking.

The terms and expressions that have been employed are used as terms of description and not of limitation, and there is no intention in the use of such terms and expressions of excluding any equivalents of the features shown and described or portions thereof, but it is recognized that various modifications are possible within the scope of the aspects of the present invention. Thus, it should be understood that although the present invention has been specifically disclosed by specific aspects and optional features, modification and variation of the concepts herein disclosed may be resorted to by those of ordinary skill in the art, and that such modifications and variations are considered to be within the scope of aspects of the present invention.

Exemplary Aspects.

The following exemplary aspects are provided, the numbering of which is not to be construed as designating levels of importance:

Aspect 1 provides a catalyst particle for catalyzing the production of syngas from carbon dioxide and methane, the catalyst particle comprising:

a metal oxide substrate comprising a particulate nickel phase, wherein an exposed surface of the catalyst particle comprises at least some of the particulate nickel phase and the exposed surface is substantially nonporous.

Aspect 2 provides the catalyst particle of Aspect 1, wherein, if present, any pore of the exposed surface is less than about 50 nm wide.

Aspect 3 provides the catalyst particle of any one of Aspects 1 or 2, wherein, if present, any pore of the exposed surface is in a range of from about 10 nm wide to about 30 nm wide.

Aspect 4 provides the catalyst particle of any one of Aspects 1-3, wherein, if present, any pore of the exposed surface is in a range of from about nm wide to about 15 nm wide.

Aspect 5 provides the catalyst particle of any one of Aspects 1-4, wherein the exposed surface is free of any pores.

Aspect 6 provides the catalyst particle of any one of Aspects 1-5, wherein, if present, any through pore of the catalyst particle is less than about 50 nm wide.

Aspect 7 provides the catalyst particle of Aspect 6, wherein, if present, any through pore of the catalyst particle is in a range of from about 10 nm wide to about 30 nm wide.

Aspect 8 provides the catalyst particle of any one of Aspects 6 or 7, wherein, if present, any through pore of the catalyst particle is in a range of from about 10 nm wide to about 25 nm wide.

Aspect 9 provides the catalyst particle of any one of Aspects 6-8, wherein, if present, any through pore of the catalyst particle is in a range of from about 10 nm wide to about 20 nm wide.

Aspect 10 provides the catalyst particle of any one of Aspects 6-9, wherein the catalyst particle is free of a through pore.

Aspect 11 provides the catalyst particle of any one of Aspects 1-10, wherein the metal oxide substrate comprises NiO, CoO, FeO, MnO, MgO, or a mixture thereof.

Aspect 12 provides the catalyst particle of any one of Aspects 1-11, wherein the metal oxide substrate comprises MgO.

Aspect 13 provides the catalyst particle of any one of Aspects 1-12, wherein the metal oxide substrate is substantially spherical, substantially cylindrical, substantially flat, or comprises an undulating profile.

Aspect 14 provides the catalyst particle of any one of Aspects 1-13, wherein the metal oxide substrate is a continuous structure.

Aspect 15 provides the catalyst particle of any one of Aspects 1-14, wherein the particulate nickel phase is 0.2 wt % to 30 wt % of the catalyst particle.

Aspect 16 provides the catalyst particle of any one of Aspects 1-15, wherein the particulate nickel phase is 14 wt % to 25 wt % of the catalyst particle.

Aspect 17 provides the catalyst particle of any one of Aspects 1-16, wherein the particulate nickel phase comprises elemental nickel, nickel oxide, or a mixture thereof.

Aspect 18 provides the catalyst particle of any one of Aspect 1-17, wherein the particulate nickel phase is homogenously distributed about the metal oxide substrate.

Aspect 19 provides the catalyst particle of any one of Aspects 1-18, wherein the particulate nickel phase is heterogeneously distributed about the metal oxide substrate.

Aspect 20 provides the catalyst particle of Aspect 19, wherein a major portion of the particulate nickel phase is located proximate to a surface of the metal oxide substrate.

Aspect 21 provides the catalyst particle of any one of Aspects 1-20, wherein at least a portion of the particulate nickel phase is exposed on a surface of the metal oxide substrate.

Aspect 22 provides the catalyst particle of Aspect 21, wherein the portion of the particulate nickel phase exposed on a surface of the metal oxide substrate is in a range of from about 10 wt % to about 30 wt % of the particulate nickel phase.

Aspect 23 provides the catalyst particle of any one of Aspects 21 or 22, wherein the portion of the particulate nickel phase exposed on a surface of the metal oxide substrate is in a range of from about 14 wt % to about 18 wt % of the particulate nickel phase.

Aspect 24 provides the catalyst particle of any one of Aspects 1-23, wherein a largest dimension of the catalyst particle is in a range of 1 mm to mm.

Aspect 25 provides the catalyst particle of any one of Aspects 1-24, wherein a largest dimension of the catalyst particle is in a range of 4 mm to 6 mm Aspect 26 provides the catalyst particle of any one of Aspects 1-25, wherein the catalyst particle further comprises potassium ions.

Aspect 27 provides the catalyst particle of Aspect 26, wherein the majority of the potassium ions are in/at a surface of the metal oxide substrate.

Aspect 28 provides the catalyst particle of any one of Aspects 26 or 27, wherein the potassium ions range from about 0.2 wt % to about 5 wt % of the catalyst particle.

Aspect 29 provides the catalyst particle of any one of Aspects 26-28, wherein the potassium ions range from about 1 wt % to about 2 wt % of the catalyst particle.

Aspect 30 provides the catalyst particle of any one of Aspects 1-29, wherein the catalyst particle comprises less than about 2 wt % free elemental nickel, free nickel oxide, or a mixture thereof in the particulate nickel phase.

Aspect 31 provides the catalyst particle of any one of Aspects 1-30, wherein the catalyst particle comprises less than about 0.5 wt % free elemental nickel, free nickel oxide, or a mixture thereof in the particulate nickel phase.

Aspect 32 provides the catalyst particle of any one of Aspects 1-31, wherein the catalyst particle is free of free elemental nickel, free nickel oxide, or a mixture thereof in the particulate nickel phase.

Aspect 33 provides the catalyst particle of any one of Aspects 1-32, wherein the catalyst particle is a solid-solution catalyst particle.

Aspect 34 provides a catalyst particle for catalyzing the production of syngas from carbon dioxide and methane, wherein the catalyst particle is a solid-solution catalyst particle formed from at least two solid reactants, and the at least two solid reactants comprise:
  atomic radii that are within about 15% of each other;
  substantially the same crystal structure;
  substantially the same electronegativity;
  substantially similar valency; or
  a combination thereof.

Aspect 35 provides the catalyst particle of Aspect 34, wherein the at least two solid reactants comprise magnesium oxide and nickel oxide.

Aspect 36 provides a method of making the catalyst particle of any one of Aspects 1-35, the method of making the catalyst particle comprising:
  mixing a nickel solution into a metal oxide powder, to form mixed powder;
  drying the mixed powder to form a dried paste;
  crushing the dried paste to form a dried powder;
  calcining the dried powder;
  forming one or more particles from the dried powder; and
  calcining the particles to form the catalyst particle.

Aspect 37 provides the method of Aspect 36, wherein the nickel solution comprises nickel(II) nitrate hexahydrate, nickel(II)di-acetate, nickel(II)carbonate, or a combination thereof.

Aspect 38 provides the method of Aspect 36 or 37, wherein the nickel solution comprises nickel(II) nitrate hexahydrate.

Aspect 39 provides the method of any one of Aspects 36-38, wherein the calcining of the dried powder occurs at a temperature in a range of from about 400° C. to about 2000° C. for a time in a range of from about 0.5 hours to about 4 hours.

Aspect 40 provides the method of any one of Aspects 36-39, wherein calcining the dried powder occurs at a temperature in a range of from about 500° C. to about 1500° C. for a time in a range of from about 1 hour to about 3 hours.

Aspect 41 provides the method of any one of Aspects 36-40, wherein calcining the dried powder occurs at a temperature in a range of from about 950° C. to about 1050° C. for a time in a range of from about 1 hour to about 3 hours.

Aspect 42 provides the method of any one of Aspects 36-41, wherein the calcining of the particles is performed at a temperature in a range of from about 800° C. to about 1500° C. for a time in a range of from about 0.5 hours to about 4 hours.

Aspect 43 provides the method of any one of Aspects 36-42, wherein calcining the dried powder occurs at a temperature in a range of from about 900° C. to about 1100° C. for a time in a range of from about 1 hour to about 3 hours.

Aspect 44 provides the method of any one of Aspects 36-43, further comprising treating the particles with potassium nitrate, potassium acetate, potassium carbonate, or a mixture thereof.

Aspect 45 provides the method of any one of Aspects 36-44, wherein a $d_{50}$ of the metal oxide powder is in a range of from about 2 μm to about 120 μm.

Aspect 46 provides the method of any one of Aspects 36-45, wherein a $d_{50}$ of the metal oxide powder is in a range of from about 5 μm to about 100 μm.

Aspect 47 provides a method of using the catalyst particle of any one of Aspects 1-46, the method comprising:
contacting the catalyst particle with methane and carbon dioxide to produce carbon monoxide and hydrogen.

Aspect 48 provides the method of using the catalyst particle of Aspect 47, wherein the carbon monoxide and hydrogen are produced in a molar ratio in a range of from about 1:1 to about 1:3.

Aspect 49 provides the method of using the catalyst particle of any one of Aspects 47 or 48, wherein the methane and carbon dioxide are supplied to the catalyst particle at a molar ratio of 5:1 to 1:5.

Aspect 50 provides the method of using the catalyst particle of any one of Aspects 47-49, wherein the methane and carbon dioxide are supplied to the catalyst particle at a molar ratio of 2:1 to 1:2.

Aspect 51 provides the method of using the catalyst particle of any one of Aspects 47-50, wherein the methane and carbon dioxide are supplied to the catalyst particle at a molar ratio of 1:1.

Aspect 52 provides the method of using the catalyst particle of any one of Aspects 47-51, further comprising activating the catalyst particle.

Aspect 53 provides the method of using the catalyst particle of Aspect 52, wherein activating the catalyst particle comprises contacting the catalyst particle with a mixture of hydrogen gas and nitrogen gas for a time in a range of from about 1 hour to about 6 hours at a temperature in a range of from about 400° C. to about 600° C., wherein a ratio of hydrogen gas to nitrogen gas is in a range of from about 90:10 to about 70:30.

Aspect 54 provides the method of using the catalyst particle of any one of Aspects 47-53, wherein at least 70 wt % of the carbon dioxide and methane that contacts the catalyst particle are converted to carbon monoxide and hydrogen per turn.

Aspect 55 provides the method of using the catalyst particle of any one of Aspects 47-54, wherein at least 90 wt % of the carbon dioxide and methane that interact with the catalyst particle are converted to carbon monoxide and hydrogen per turn.

Aspect 56 provides the method of using the catalyst particle of any one of Aspects 47-55, wherein about 70 wt % to about 99 wt % of the carbon dioxide and methane that interact with the catalyst particle are converted to carbon monoxide and hydrogen per turn.

Aspect 57 provides the method of using the catalyst particle of any one of Aspects 47-56, wherein about 90 wt % to about 99 wt % of the carbon dioxide and methane that interact with the catalyst particle are converted to carbon monoxide and hydrogen per turn.

Aspect 58 provides the method of using the catalyst particle of any one of Aspects 47-57, wherein about 95 wt % to about 98 wt % of the carbon dioxide and methane that interact with the catalyst particle are converted to carbon monoxide and hydrogen per turn.

Aspect 59 provides the method of using the catalyst particle of any one of Aspects 47-58, wherein the catalyst particle performs at a turnover frequency of about 2000 to about 20000.

Aspect 60 provides the method of using the catalyst particle of any one of Aspects 47-59, wherein the catalyst particle performs at a turnover frequency of about 3000 to about 5000.

Aspect 61 provides the method of using the catalyst particle of any one of Aspects 47-60, wherein the reaction is performed at a temperature in a range of from about 530° C. to about 1100° C.

Aspect 62 provides the method of using the catalyst particle of any one of Aspects 47-61, wherein the reaction is performed at a temperature in a range of from about 800° C. to about 990° C.

Aspect 63 provides the method of using the catalyst particle of any one of Aspects 47-62, wherein the catalyst particle is substantially free of coking during performance of the method.

Aspect 64 provides the method of using the catalyst particle of any one of Aspects 47-63, wherein the catalyst particle is substantially free of coking during performance of the method with continuous operation for at least 1 year.

Aspect 65 provides the method of using the catalyst particle of any one of Aspects 47-64, wherein the catalyst particle is substantially free of coking during continuous operation for at least 2 years.

Aspect 66 provides the method of using the catalyst particle of any one of Aspects 47-65, wherein the catalyst particle is substantially free of coking during continuous operation for at least 3 years.

Aspect 67 provides the method of using the catalyst particle of any one of Aspects 47-66, wherein the carbon dioxide, the methane, or both are provided from an industrial emission, an air captured carbon source, or both.

Aspect 68 provides the method of using the catalyst particle of any one of Aspects 47-67, wherein the methane and carbon dioxide are contacted with the catalyst particle a pressure in a range of from about 25 KPa to about 2500 KPa.

Aspect 69 provides the method of using the catalyst particle of any one of Aspects 47-68, wherein the methane and carbon dioxide are contacted with the catalyst particle a pressure in a range of from about 30 KPa to about 2100 KPa.

Aspect 70 provides the method of using the catalyst particle of any one of Aspects 47-69, wherein a feed stream comprising the methane and carbon dioxide has a flow rate, measured as gas hourly space velocity (GHSV), of from about 500 $h^{-1}$ to about 15000 $h^{-1}$.

Aspect 71 provides the method of using the catalyst particle of any one of Aspects 47-70, wherein a feed stream comprising the methane and carbon dioxide has a flow rate, measured as gas hourly space velocity (GHSV), of from about 1000 $h^{-1}$ to about 10000 $h^{-1}$.

Aspect 72 provides the method of any one of Aspects 47-71, further comprising treating the catalyst particle with steam before or after producing syngas.

Aspect 73 provides the method of Aspect 72, wherein the catalyst particle is treated with steam at a temperature in a range of from about 150° C. to about 300° C. for 1 hour to 20 hours.

Aspect 74 provides the method of any one of Aspects 72 or 73, wherein the catalyst particle is treated with steam at a temperature in a range of from about 200° C. to about 260° C. from 2 hours to 15 hours.

Aspect 75 provides the method of any one of Aspects 47-74, wherein the method comprises a dry reforming method.

Aspect 76 provides the method of any one of Aspects 47-75, wherein the method is not a steam reforming method.

Aspect 77 provides the method of any one of Aspects 47-76, further comprising supplementing the produced carbon monoxide and hydrogen with an external source of hydrogen.

Aspect 78 provides the method of Aspect 77, wherein the external source of hydrogen is a renewable source of hydrogen.

Aspect 79 provides the method of Aspect 78, wherein the renewable source of hydrogen is produced by electrolysis.

Aspect 80 provides a method of using syngas produced according to any one of Aspects 47-79, the method comprising:
forming a product from a feedstock comprising the syngas.

Aspect 81 provides the method of using syngas of Aspect 80, wherein the product comprises a paraffinic base oil, a paraffinic wax, a solvent, a fuel, ammonia, methanol, ethanol, propanol, butanol, pentanol, acetic acid, dimethoxyethane, or a mixture thereof.

Aspect 82 provides the method of using syngas of any one of Aspects 80 or 81, wherein the syngas is directly fed into the method for forming the product.

Aspect 83 provides a product comprising about 40 wt % to about 100 wt % carbon produced from the method of any one of Aspects 47-82

Aspect 84 provides the product of Aspect 83, comprising about wt % to about 100 wt % carbon produced from the method of any one of Aspects 47-80

Aspect 85 provides the product of any one of Aspects 84 or 85, comprising about 70 wt % to about 100 wt % carbon produced from the method of any one of Aspects 47-81

Aspect 86 provides the product of any one of Aspects 83-85, wherein about 40 wt % to about 80 wt % of the carbon produced from the method of any one of Aspects 47-81 is from a source of carbon dioxide emission.

Aspect 87 provides the product of any one of Aspects 83-86, wherein about 70 wt % to about 80% of the carbon produced from the method of any one of Aspects 47-81 is from a source of carbon dioxide emission.

Aspect 88 provides an assembly comprising:
a reaction vessel comprising the catalyst particle of any one of Aspects 1-87 located within the reaction vessel.

Aspect 89 provides the assembly of Aspect 88, wherein the reaction vessel comprises a metal tube.

Aspect 90 provides the assembly of Aspect 89, wherein the metal tube comprises a nickel alloy.

Aspect 91 provides the assembly of any one of Aspects 88-90, wherein the tube comprises a plurality of the catalyst particles evenly distributed about an interior of the tube.

Aspect 92 provides the assembly of any one of Aspects 83-91, further comprising a heat source in thermal communication with the reaction vessel.

Aspect 93 provides the assembly of Aspect 92, further comprising a feedback loop to direct carbon dioxide produced by the heat source to the reaction vessel to participate in the method of any one of Aspects 47-87.

Aspect 94 provides the assembly of any one of Aspects 83-93, further comprising a feed source of carbon dioxide that is captured from an industrial emission a direct air capture source, or both.

What is claimed is:

1. A catalyst particle for catalyzing the production of syngas from carbon dioxide and methane, the catalyst particle comprising:
a metal oxide substrate comprising a particulate nickel phase, wherein an exposed surface of the catalyst particle comprises at least some of the particulate nickel phase and the catalyst particle comprises a low porosity,
wherein at least 51 wt % of the particulate nickel phase is located proximate to a surface of the metal oxide substrate.

2. The catalyst particle of claim 1, wherein the metal oxide substrate comprises NiO, CoO, FeO, MnO, MgO, or a mixture thereof.

3. The catalyst particle of claim 1, wherein the metal oxide substrate comprises MgO.

4. The catalyst particle of claim 1, wherein the particulate nickel phase is 0.2 wt % to 30 wt % of the catalyst particle.

5. The catalyst particle of claim 1, wherein the particulate nickel phase comprises elemental nickel, nickel oxide, or a mixture thereof.

6. The catalyst particle of claim 1, wherein the catalyst particle comprises less than about 0.5 wt % free elemental nickel, free nickel oxide, or a mixture thereof in the particulate nickel phase.

7. The catalyst particle of claim 1, wherein the catalyst particle is a solid-solution catalyst particle.

8. A method of using a catalyst particle, the method comprising:
contacting the catalyst particle of claim 1 with methane and carbon dioxide to produce carbon monoxide and hydrogen.

9. The method of using the catalyst particle of claim 8, wherein the carbon monoxide and the hydrogen are produced in a molar ratio in a range of from about 1:1 to about 1:3.

10. The method of using the catalyst particle of claim 8, wherein at least 70 percent of a total weight of the carbon dioxide and the methane that contacts the catalyst particle are converted to carbon monoxide and hydrogen per turn.

11. The method of using the catalyst particle of claim 8, wherein at least 90 percent of a total weight of the carbon dioxide and the methane that interact with the catalyst particle are converted to carbon monoxide and hydrogen per turn.

12. The method of using the catalyst particle of claim 8, wherein the catalyst particle is substantially free of coking during performance of the method.

13. The method of using the catalyst particle of claim 8, further comprising forming a product from a feedstock comprising syngas.

14. The method of using the catalyst particle of claim 13, wherein the product comprises a paraffinic base oil, a paraffinic wax, a solvent, a fuel, ammonia, methanol, ethanol, propanol, butanol, pentanol, acetic acid, dimethoxyethane, or a mixture thereof.

15. The method of using the catalyst particle of claim 8, further comprising contacting the catalyst particle with air, steam, or a mixture thereof to clean the catalyst particle.

16. The method of claim 15, wherein the air, steam, or the mixture thereof is intermittently contacted with the catalyst particle.

* * * * *